United States Patent [19]

Haga et al.

[11] Patent Number: 5,256,674
[45] Date of Patent: Oct. 26, 1993

[54] IMIDAZOLIDINE DERIVATIVES, PROCESS FOR PRODUCING THE SAME AND PESTICIDES CONTAINING THE SAME

[75] Inventors: Takahiro Haga; Tadaaki Toki; Toru Koyanagi; Masato Omatsu; Hiroshi Sasaki; Masayuki Morita; Kiyomitsu Yoshida, all of Kusatsu, Japan

[73] Assignee: Ishihara Sangyo Kaisha Ltd., Osaka, Japan

[21] Appl. No.: 631,992

[22] Filed: Dec. 21, 1990

[30] Foreign Application Priority Data

Dec. 28, 1989 [JP] Japan .................................. 1-340373
Mar. 29, 1990 [JP] Japan .................................. 2-82600

[51] Int. Cl.$^5$ ................ A01N 43/40; C07D 401/06
[52] U.S. Cl. ................................ 514/341; 514/333; 514/336; 514/401; 514/402; 514/365; 546/276; 546/278; 546/256; 546/261; 546/262; 546/263; 548/202
[58] Field of Search ............. 546/278, 276, 256, 261, 546/262, 263; 514/341, 402, 401, 336, 713, 333

[56] References Cited

U.S. PATENT DOCUMENTS

| | | | |
|---|---|---|---|
| 3,940,484 | 2/1976 | Baker et al. | 514/322 |
| 4,725,589 | 2/1988 | Tsuboi et al. | 514/128 |
| 4,742,060 | 5/1988 | Shiokawa et al. | 514/341 |
| 4,831,036 | 5/1989 | Wolf et al. | 514/258 |

FOREIGN PATENT DOCUMENTS 0192060 8/1986 European Pat. Off.
0292822 11/1988 European Pat. Off.

*Primary Examiner*—Richard L. Raymond
*Assistant Examiner*—Shailendra Kumar
*Attorney, Agent, or Firm*—Oblon, Spivak, McClelland, Maier & Neustadt

[57] ABSTRACT

An imidazolidine derivative having the formula (I) or its salt:

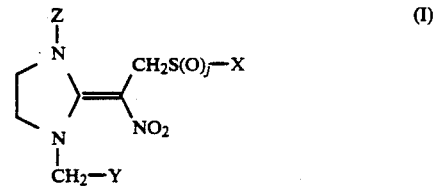

wherein X is an alkyl group which may be substituted, an alkenyl group which may be substituted, an alkynyl group which may be substituted,

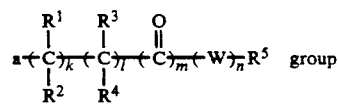

(in which each of $R^1$, $R^2$, $R^3$ and $R^4$ is independently a hydrogen atom or an alkyl group, $R^5$ is an alkyl group which may be substituted with a halogen atom, a cycloalkyl group which may be substituted or a phenyl group which may be substituted, W is an oxygen atom or a sulfur atom, and each of k, l, m and n is independently 0 or 1, provided that (a) case where all of k, l and m are 0 at the same time and (b) case where m and n are 0 at the same time and $R^5$ is an alkyl group which may be substituted with a halogen atom, are excluded), or

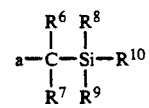

group (in which each of $R^6$ and $R^7$ is independently a hydrogen atom or an alkyl group, each of $R^8$ and $R^9$ is independently an alkyl gorup, $R^{10}$ is an alkyl group which may be substituted, an aryl group which may be substituted, a pyridyl group which may be substituted, an alkenyl group which may be substituted with a halogen atom or an alkynyl group which may be substituted with a halogen atom); Y is a 6-chloro-3-pyridyl group or a 2-chloro-5-thiazolyl group; Z is a hydrogen atom, an alkyl group or an acyl group; and j is an integer of from 0 to 2.

9 Claims, No Drawings

IMIDAZOLIDINE DERIVATIVES, PROCESS FOR PRODUCING THE SAME AND PESTICIDES CONTAINING THE SAME

The present invention relates to novel imidazolidine derivatives, a process for producing the same and pesticides containing the same.

Imidazolidine derivatives are known from the following prior arts.

For example, U.S. Pat. Nos. 4,731,385, 4,767,864, 4,831,036, 4,725,589, 4,780,457, 4,772,620, 4,812,454, 4,647,570, 4,680,294, 4,678,795, 4,774,247 and 4,812,571 disclose a compound having the formula,

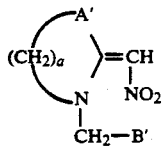

(wherein A' is an NH group or the like, B' is a pyridyl or thiazolyl group which may be substituted, and a is an integer of from 2 to 4), which is different from the compound of the present invention in respect that the carbon atom having a nitro group in the cited compound has a hydrogen atom.

EP-A-292822 discloses a compound having the formula,

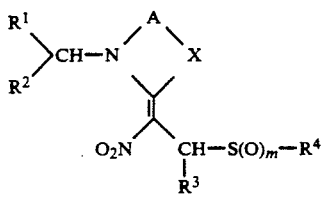

(wherein A is an alkanediyl group; X is an N-R$^5$ group in which R$^5$ is a hydrogen atom, an alkyl, alkenyl, alkynyl, acyl or alkoxycarbonyl group which may be substituted, or the like; R$^1$ is a pyridyl or thiazolyl group which may be substituted, or the like; R$^2$ is a hydrogen atom or an alkyl group; R$^3$ is a hydrogen atom or the like; and R$^4$ is a phenyl, naphthyl, pyridynyl or pyrimidynyl group which may be substituted, an imidazolyl group or a triazolyl group), which is different from the compound of the present invention in respect that R$^4$ has a cyclic group.

EP-A-259738 (corresponding to U.S. Pat. Nos. 4,803,277 and 4,882,344) discloses a compound having the formula,

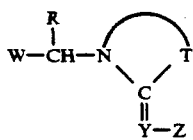

(wherein W is a pyridyl or thiazolyl group which may be substituted, or the like; R is a hydrogen atom or the like; T forms a 5- or 6-membered unsaturated heterocyclic ring together with adjacent carbon atom and nitrogen atom; Z is a nitro group, or the like; and Y is a =CR'— group in which R' is a hydrogen atom, an alkyl group, an aryl group, an acyl group, an alkoxycarbonyl group or a cyano group, or the like), which is different from the compound of the present invention in respect that T forms an unsaturated heterocyclic ring and that R' in Y is different.

EP-A-192060 (corresponding to U.S. Pat. No. 4,845,106) discloses a compound having the formula,

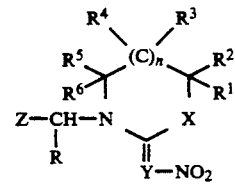

(wherein n is 0 or 1; R$^1$, R$^2$, R$^3$, R$^4$, R$^5$ and R$^6$ are a hydrogen atom or the like; Z is a pyridyl or thiazolyl group which may be substituted, or the like; R is a hydrogen atom or the like; X is an N—R$^7$ group in which R$^7$ is a hydrogen atom, an alkyl, alkenyl, alkynyl, acyl or alkoxycarbonyl group which may be substituted, or the like; and Y is a CR$^9$ group in which R$^9$ is a hydrogen atom or an alkyl group which may be substituted with a halogen atom, a hydroxyl group or an alkylthio group, or the like). The cited compound expressed by the above general formula partly includes a part of the compounds of the present invention when X in the above general formula is an N—R$^7$ group and R$^9$ in Y is an alkyl group substituted with an alkylthio group. However, this reference discloses nothing about concrete examples for the part of the compounds of the present invention, which is considered to be included by the above general formula.

An object of the present invention is to provide imidazolidine derivatives having the following general formula (I) or their salts, a process for producing the same and a pesticide containing the same.

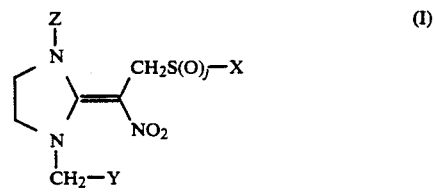

wherein X is an alkyl group which may be substituted, an alkenyl group which may be substituted, an alkynyl group which may be substituted,

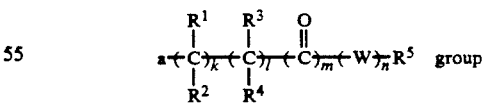

(in which each of R$^1$, R$^2$, R$^3$ and R$^4$ is independently a hydrogen atom or an alkyl group; R$^5$ is an alkyl group which may be substituted with a halogen atom, a cycloalkyl group which may be substituted or a phenyl group which may be substituted; W is an oxygen atom or a sulfur atom; and each of k, l, m and n is independently an integer of 0 or 1, provided that (a) case where all of k, l and m are 0 at the same time and (b) case where m and n are 0 at the same time and R$^5$ is an alkyl group which may be substituted with a halogen atom, are excluded), or

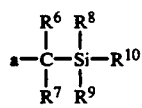

group (in which $R^6$ and $R^7$ are respectively and independently a hydrogen atom or an alkyl group; each of $R^8$ and $R^9$ is independently an alkyl group; $R^{10}$ is an alkyl group which may be substituted, an aryl group which may be substituted, a pyridyl group which may be substituted, an alkenyl group which may be substituted with a halogen atom or an alkynyl group which may be substituted with a halogen atom); Y is a 6-chloro-3-pyridyl group or a 2-chloro-5-thiazolyl group; Z is a hydrogen atom, an alkyl group or an acyl group; and j is an integer of from 0 to 2.

Among the imidazolidine derivatives or their salts, preferable examples include a compound wherein Y is a 6-chloro-3-pyridyl group and a compound wherein j is 0, and more preferable examples include a compound wherein X is an allyl group, Y is a 6-chloro-3-pyridyl group, Z is a hydrogen atom and j is 0; a compound wherein X is a 2-methyl- 2-propenyl group, Y is a 6-chloro-3-pyridyl group, Z is a hydrogen atom and j is 0; and a compound wherein X is a dimethylphenylsilylmethyl group, Y is a 6-chloro-3-pyridyl group, Z is a hydrogen atom and j is 0.

In the above general formula (I), X and $R^{10}$ include an alkenyl or alkynyl group having a carbon number of from 2 to 6 such as a vinyl group, a propenyl group, a butenyl group, a pentenyl group, a hexenyl group, an ethynyl group, a propynyl group, a butynyl group, a pentynyl group, a hexynyl group or the like, and they further include structural isomers of a linear or branched aliphatic chain. $R^5$ includes a cycloalkyl group having a carbon number of from 3 to 6 such as a cyclopropyl group, a cyclobutyl group, a cyclopentyl group, a Cyclohexyl group or the like, and $R^{10}$ includes an aryl group such as a phenyl group, a naphthyl group or the like. Z includes an acyl group such as a formyl group, an acetyl group or the like.

Furthermore, in the above general formula (I), X includes an alkyl group which may be substituted, an alkenyl group which may be substituted and an alkynyl group which may be substituted, but their substituents include a halogen atom, a

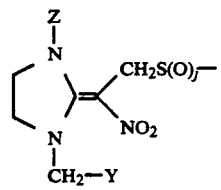

group (Y, Z and j are as defined above) or the like; $R^5$ may further include a phenyl group which may be substituted and $R^{10}$ may further include an aryl group which may be substituted and a pyridyl group which may be substituted, but their substituents include a halogen atom, an alkyl group which may be substituted with a halogen atom, an alkenyl group which may be substituted with a halogen atom, an alkynyl group which may be substituted with a halogen atom, an alkoxy group which may be substituted with a halogen atom, an alkoxycarbonyl group which may be substituted with a halogen atom, a phenoxy group which may be substituted, a phenyl group which may be substituted, a pyridyloxy group which may be substituted or the like (the substituents of the phenoxy group which may be substituted, the phenyl group which may be substituted and the pyridyloxy group which may be substituted include a halogen atom, an alkyl group which may be substituted with a halogen atom or the like). Still further, $R^5$ may further include a cycloalkyl group which may be substituted, but its substituents include a halogen atom, an alkyl group which may be substituted with a halogen atom or the like; and RID may further include an alkyl group which may be substituted, but its substituents include a halogen atom, a phenyl group or the like.

When the alkyl group which may be substituted, the alkyl group which may be substituted with a halogen atom, the alkoxy group which may be substituted with a halogen atom, the alkenyl group which may be substituted, the alkenyl group which may be substituted with a halogen atom, the alkynyl group which may be substituted with a halogen atom, the phenyl group which may be substituted, the aryl group which may be substituted, the pyridyl group which may be substituted, the cycloalkyl group which may be substituted, the alkoxycarbonyl group which may be substituted with a halogen atom, the phenoxy group which may be substituted and the pyridyloxy group which may be substituted, in the above general formula, has two or more substituents, they may be the same or different.

The alkyl group and the alkyl moiety of the alkoxy group in the above general formula (I) contain from 1 to 6 carbon atoms, examples of which include a methyl group, an ethyl group, a propyl group, a butyl group, a pentyl group, a hexyl group or the like, and their structural isomers of a linear or branched aliphatic chain.

Examples of the halogen atoms in the above general formula (I) include a fluorine atom, a chlorine atom, a bromine atom and a iodine atom. Examples of the salt of the compound having the above general formula (I) include a salt with an acidic substance, e.g. an inorganic acid salt such as a hydrochloride, a hydrobromide, a phosphate, a sulfate, a nitrate or the like.

The compounds having the above-mentioned general formula (I) include E-form and Z-form isomers, and the present invention involves E-form, Z-form and a mixture thereof.

The compound having the above-mentioned general formula (I) can be prepared, for example, by the following processes.

(i) When Z is a hydrogen atom and j is 0:

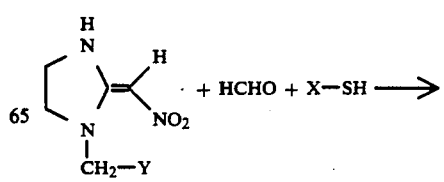

-continued

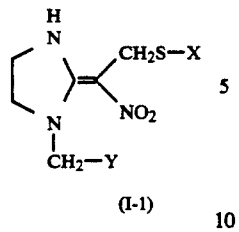

(I-1)

(wherein X and Y are as defined above).

The above reaction is carried out generally in the presence of a solvent. Examples of the solvent include water, alcohols such as methanol, ethanol, propanol, isopropanol, butanol or t-butanol, and a mixture thereof.

The reaction temperature of the above reaction is generally from 20 to 120° C, preferably from 40 to 100° C, and the reaction time is from 0.5 to 6 hours.

Formaldehyde used in the above reaction is used generally in the form of an aqueous solution, but paraformaldehyde in the form of powder can also be used.

(ii) When Z is a hydrogen atom and j is 1 or 2:

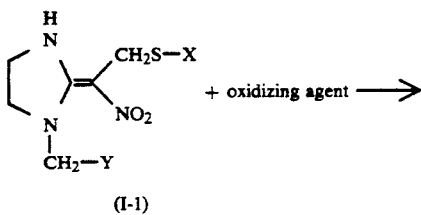

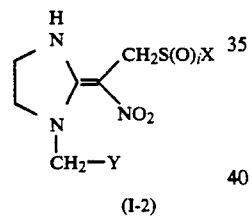

(I-2)

(wherein X and Y are as defined above, and i is an integer of 1 or 2).

Examples of the oxidizing agent used in the above reaction include hydrogen peroxide, m-chloroperbenzoic acid or the like.

The above reaction is carried out usually in the presence of a solvent, examples of which include carboxylic acids such as acetic acid, halogenated hydrocarbons such as methylene chloride or chloroform, and the like.

The reaction temperature of the above reaction is generally from 0° to 110° C, preferably from 10° to 100° C, and the reaction time is generally from 1 to 24 hours, preferably from 2 to 12 hours.

In the above reaction, when the oxidizing agent is used in the same molar amount as the compound having the formula (I-1), the compound having the formula (I-2) chloroform or the like. Examples of the base include alkali metal hydrides such as sodium hydride, potassium hydride or the like, organic lithium compounds such as n-butyl lithium, phenyl lithium or the like, organic bases such as triethylamine, pyridine or the like, and alkali metal hydroxides such as sodium hydroxide, potassium hydroxide or the like.

The reaction temperature of the above reaction is generally from −20° to 100° C., preferably from 10 to 50° C., and the reaction time is generally from 0.25 to 24 hours, preferably from 0.5 to 12 hours.

Synthesis Examples of the compounds of the present invention are illustrated hereinafter.

SYNTHESIS EXAMPLE 1

Synthesis of 1-(6-chloro-3-pyridylmethyl)-2-(1-nitro-2-ethoxycarbonylmethylthioethylidene)imidazolidine (Compound No. 1)

0.22 g of 1-(6-chloro-3-pyridylmethyl)-2-nitromethyleneimidazolidine, 0.08 g of 37% formaldehyde aqueous solution and 0.1 g of ethyl thioglycolate were added to 5 ml of ethanol, and were reacted under reflux for 3 hours. After completing the reaction, ethanol was distilled off under reduced pressure, and a small amount of ethyl acetate was added to the residue thus obtained to filter the insoluble materials out, thus obtaining 0.25 g of the aimed product (Compound No. 1) having a melting point of from 122.8° to 124.3° C. wherein i is 1, can be obtained, and when the oxidizing agent is used in a molar amount of two times as large as the compound having the formula (I-1), the compound having the formula (I-2) wherein i is 2, can be obtained. (iii) When Z is an alkyl group or an acyl group:

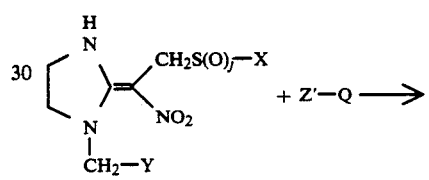

(I-3)

(I-4)

(wherein X, Y and j are as defined above; Z' is an alkyl group or an acyl group; and Q is a halogen atom or an acid residue).

Examples of the acid residue represented by Q include residues of carboxylic acid, sulfonic acid or the like.

The above reaction is carried out generally in the presence of a solvent and a base. Examples of the solvent include aprotic polar solvents such as N,N-dimethylformamide, acetonitrile or the like, ethers such as tetrahydrofuran, 1,4-dioxane or the like, and halogenated hydrocarbons such as methylene chloride,

SYNTHESIS EXAMPLE 2

Synthesis of 1-(6-chloro-3-pyridylmethyl)-2-(1-nitro-2-allylthioethylidene)imidazolidine (Compound No. 3)

0.5 g of 1-(6-chloro-3-pyridylmethyl)-2-nitromethyleneimidazolidine, 0.19 g of 37% formaldehyde aqueous solution and 0.22 g of allylmercaptan were added to 10 ml of ethanol, and were reacted under reflux for 2 hours. After completing the reaction, ethanol was distilled off under reduced pressure, and a small amount of ethyl acetate was added to the residue thus obtained to filter the insoluble materials out, thus obtaining 0.33 g of the aimed product (Compound No. 3) having a melting point of from 134.0° to 135.0° C.

SYNTHESIS EXAMPLE 3

Synthesis of 1-(6-chloro-3-pyridylmethyl)-2-(1-nitro-2-trimethyl-silylmethylthioethylidene)imidazolidine (Compound No. 20)

0.5 g of 1-(6-chloro-3-pyridylmethyl)-2-nitromethyleneimidazolidine, 0.18 g of 37% formaldehyde aqueous solution and 0.24 g of mercaptomethyl trimethylsilane were added to 15 ml of ethanol, and were reacted under reflux for 1 hour. After completing the reaction, the reaction liquor was cooled by ice to precipitate a crystal. The crystal thus precipitated was taken out by filtration, and was washed with a cold ethanol to obtain 0.3 g of the aimed product (Compound No. 20) having a melting point of from 162.3° to 164.3° C.

SYNTHESIS EXAMPLE 4

Synthesis of 1-(6-chloro-3-pyridylmethyl)-2-(1-nitro-2-dimethylphenylsilylmethylthioethylidene)imidazolidine (Compound No. 21)

0.5 g of 1-(6-chloro-3-pyridylmethyl)-2-nitromethyleneimidazolidine, 0.16 g of 37% formaldehyde aqueous solution and 0.4 g of mercaptomethylphenyl dimethylsilane were added to 10 ml of ethanol, and were reacted under reflux for 1 hour. After completing the reaction, the reaction solution was cooled by ice to precipitate a crystal, and the crystal thus precipitated was washed with a cold ethanol to obtain 0.3 g of the aimed product (Compound No. 21) having a melting point of from 138.3° to 138.8° C.

SYNTHESIS EXAMPLE 5

Synthesis of 1-(6-chloro-3-pyridylmethyl)-3-methyl-2-(1-nitro-2-allylthioethylidene)imidazolidine (Compound No. 63)

0.5 g of 1-(6-chloro-3-pyridylmethyl)-2-(1-nitro-2-allylthioethylidene)imidazolidine was dissolved in 10 ml of N,N-dimethylformamide, and 0.06 g of sodium hydride (60% oil suspension) was then gradually added thereto at room temperature. The resultant reaction liquor was continuously stirred for about 15 minutes until the generation of hydrogen gas stopped, and thereafter 0.18 g of methyl iodide was gradually added dropwise to the reaction liquor. The reaction liquor was further continuously stirred for 2 hours at room temperature, and the solvent was then distilled off under reduced pressure to obtain a residue. The residue thus obtained was purified by silica gel column chromatography (eluting solution: ethyl acetate/methanol =2/1) to obtain 0.26 g of the desired compound (Compound No. 63) having a refractive index of $n_D^{39.0} = 1.6205$.

Typical examples of the compounds represented by the above general formula (I) are listed in the following Tables 1 and 2.

TABLE 1

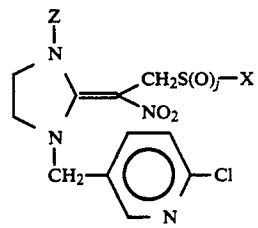

(I-5)

| Compound No. | X | Z | j | Physical properties |
|---|---|---|---|---|
| 1 | —CH$_2$CO$_2$C$_2$H$_5$ | H | 0 | m.p. 122.8–124.3° C. |
| 2 | —CH$_2$C$_6$H$_5$ | H | 0 | m.p. 172.0–175.0° C. |
| 3 | —CH$_2$—CH=CH$_2$ | H | 0 | m.p. 134.0–135.0° C. |
| 4 | —CH$_2$CH$_3$ | H | 0 | m.p. 137.0–138.0° C. |
| 5 | -t-C$_4$H$_9$ | H | 0 | m.p. 167.0–168.0° C. |
| 6 | —C(CH$_3$)$_2$—CO$_2$C$_6$H$_5$ | H | 0 | m.p. 128.3–129.8° C. |
| 7 | —CO—C$_6$H$_5$ | H | 0 | Amorphous solid |
| 8 | —CH$_2$—C(CH$_3$)=CH$_2$ | H | 0 | m.p. 151.4–152.0° C. |
| 9 | —CH$_2$—C≡CH | H | 0 | m.p. 143.4–144.4° C. |
| 10 | —CH(CH$_3$)CO$_2$CH$_3$ | H | 0 | m.p. 137.8–139.3° C. |
| 11 | —COCH$_3$ | H | 0 | — |

TABLE 1-continued (I-5)

[Structure: Pyridine-containing cyclic compound with Z-N, CH₂S(O)ⱼ-X, NO₂, and CH₂-(2-chloropyridin-5-yl) substituents]

| Compound No. | X | Z | j | Physical properties |
|---|---|---|---|---|
| 12 | —CO—C₆H₄—CF₃ | H | 0 | — |
| 13 | —CO—C₆H₄—F | H | 0 | — |
| 14 | —CO—C₆H₄—Cl | H | 0 | — |
| 15 | —CH₂COCH₃ | H | 0 | — |
| 16 | —CH₂COC₆H₅ | H | 0 | — |
| 17 | —CH₂CH₂CH₂F | H | 0 | m.p. 107.0–109.0° C. |
| 18 | —CH₂—C≡C—I | H | 0 | — |
| 19 | —CH₂—CF=CF₂ | H | 0 | — |
| 20 | —CH₂—Si(CH₃)₃ | H | 0 | m.p. 162.3–164.3° C. |
| 21 | —CH₂—Si(CH₃)₂—C₆H₅ | H | 0 | m.p. 138.3–138.8° C. |
| 22 | —CH₂—Si(CH₃)₂—C₆H₄—OCH₃ | H | 0 | m.p. 137.3–140.3° C. |
| 23 | —CH₂—Si(CH₃)₂—C₆H₄—CH₃ | H | 0 | m.p. 142.3–143.3° C. |
| 24 | —CH₂—Si(CH₃)₂—C₆H₄—F | H | 0 | m.p. 139.8–140.8° C. |
| 25 | —CH₂—Si(CH₃)₂—C₆H₄—CF₃ | H | 0 | m.p. 154.3–155.8° C. |

TABLE 1-continued (I-5)

[Structure: 1,3-diazinane ring with N-Z at top, =C with CH₂S(O)ⱼ-X substituent, =NO₂, N-CH₂-(2-chloropyridin-5-yl)]

| Compound No. | X | Z | j | Physical properties |
|---|---|---|---|---|
| 26 | -CH₂-Si(CH₃)₂-C₆H₄-Cl | H | 0 | m.p. 140.3–142.3° C. |
| 27 | -CH₂-Si(CH₃)₂-C₆H₄-C₆H₅ | H | 0 | m.p. 163.3–164.3° C. |
| 28 | -CH₂-Si(CH₃)₂-C₆H₄-O-C₆H₅ | H | 0 | m.p. 129.8–130.8° C. |
| 29 | -CH₂-Si(CH₃)₂-(pyridyl-CF₃) | H | 0 | m.p. 125.0–129.0° C. |
| 30 | -CH₂-C≡C-CH₃ | H | 0 | m.p. 154.3–155.8° C. |
| 31 | -CH₂-cyclohexyl | H | 0 | m.p. 168.3–169.8° C. |
| 32 | -CH₂-CH₂-OCH₃ | H | 0 | m.p. 144.8–146.8° C. |
| 33 | -CH₂-C₆H₄-Cl | H | 0 | m.p. 175.2–175.6° C. |
| 34 | -CH₂-C₆H₄-CH₃ | H | 0 | m.p. 168.0–168.2° C. |
| 35 | -CH₂-C₆H₄-F | H | 0 | m.p. 174.8–175.2° C. |
| 36 | -CH(CH₃)-C₆H₅ | H | 0 | m.p. 141.6–142.2° C. |
| 37 | -CH₂-C₆H₄-CF₃ | H | 0 | m.p. 173.8–174.3° C. |

TABLE 1-continued (I-5)

[Structure: 1,3-diazinane ring with N-Z (top), N-CH2-(6-chloropyridin-3-yl) (bottom), and =C(NO2)-CH2S(O)j-X exocyclic substituent]

| Compound No. | X | Z | j | Physical properties |
|---|---|---|---|---|
| 38 | —CH2—(2-fluorophenyl) | H | 0 | m.p. 179.7–180.0° C. |
| 39 | —CH2—(4-methoxyphenyl) | H | 0 | m.p. 169.6–169.9° C. |
| 40 | —CH2—C(CH3)2—phenyl | H | 0 | m.p. 129.3–131.3° C. |
| 41 | —CH2—Si(CH3)2—(phenyl)—O—(2-chloro-4-trifluoromethylphenyl) | H | 0 | — |
| 42 | —CH2—Si(CH3)2—(2,6-dichlorophenyl)—O—(3-chloro-5-trifluoromethylpyridin-2-yl) | H | 0 | — |
| 43 | —CH2—Si(CH3)2—(2-chloro-4-trifluoromethylphenyl) | H | 0 | — |
| 44 | —CH2—Si(CH3)2—(naphthalen-2-yl) | H | 0 | — |
| 45 | —CH2—CH(CH3)—phenyl | H | 0 | — |
| 46 | —CH2—Si(CH3)2—(2-chloro-4-trifluoromethoxyphenyl) | H | 0 | — |

TABLE 1-continued (I-5)

Structure: pyridine-chloro-CH₂-N(ring with Z-N)-C(=)-CH₂S(O)ⱼ-X with NO₂ group

| Compound No. | X | Z | j | Physical properties |
|---|---|---|---|---|
| 47 | -CH₂-Si(CH₃)₂-(2-Cl,4-CF₃-pyridyl) | H | 0 | — |
| 48 | -CH₂-Si(CH₃)₂-C₆H₄-OCF₃ | H | 0 | — |
| 49 | -CH₂-Si(CH₃)₂-C₂H₅ | H | 0 | — |
| 50 | -CH₂-Si(CH₃)₂-(5-Cl-pyridyl) | H | 0 | — |
| 51 | -CH₂-Si(C₂H₅)₂-C₆H₅ | H | 0 | — |
| 52 | -CH₂-Si(C₃H₇)₂-C₆H₅ | H | 0 | — |
| 53 | -CH₂-C₆H₄-CO₂-C(CH₃)₃ | H | 0 | m.p. 150.3–151.8° C. |
| 54 | -CH₂-C₆H₄-CH=CH₂ | H | 0 | m.p. 98–101° C. |
| 55 | -CH₂-Si(CH₃)₂-CH₂-C₆H₅ | H | 0 | m.p. 138–141° C. |
| 56 | -CH₂-Si(CH₃)₂-CH=CH₂ | H | 0 | m.p. 140–142° C. |
| 57 | -CH₂CH₂SCH₃ | H | 0 | m.p. 121–122° C. |
| 58 | -CH₂CH₂SCH₂CH₃ | H | 0 | m.p. 121–122° C. |

TABLE 1-continued (I-5)

Structure: imidazolidine ring with Z-N, =C(NO₂)-CH₂S(O)ⱼ-X, and N-CH₂-(2-chloropyridin-5-yl)

| Compound No. | X | Z | j | Physical properties |
|---|---|---|---|---|
| 59 | —CH₂—Si(CH₃)₂—(3-Cl,5-CF₃-phenyl) | H | 0 | m.p. 124–126° C. |
| 60 | —CH₂CF₃ | H | 0 | m.p. 139–142° C. |
| 61 | —CH₂CH₂F | H | 0 | m.p. 128.0–129.6° C. |
| 62 | —CH₂—(4-Cl-phenyl) | H | 2 | Amorphous solid |
| 63 | —CH₂—CH=CH₂ | CH₃ | 0 | Refractive index $n_D^{39.0}$ 1.6205 |
| 64 | —CH₂—CH=CHCl | H | 0 | m.p. 144.2–144.4° C. |
| 65 | —CH₂CH₂—S—CH₂—C(NO₂)=C(NH)—N(CH₂-(2-chloropyridin-5-yl))-(imidazolidine) | H | 0 | m.p. 165.3–166.3° C. |
| 66 | —CH₂—CH=CH₂ | CHO | 0 | — |
| 67 | —CH₂—CH=CH₂ | CH₃CO | 0 | — |
| 68 | —CH₂—C(CH₃)=CH₂ | CHO | 0 | — |
| 69 | —CH₂—Si(CH₃)₂—phenyl | CHO | 0 | — |
| 70 | —CH₂—CH₂—S—CH₃ | CHO | 0 | — |

TABLE 2

(I-6)

Structure: imidazolidine ring with Z-N, =C(NO₂)-CH₂S(O)ⱼ-X, and N-CH₂-(2-chlorothiazol-5-yl)

| Compound No. | X | Z | j | Physical properties |
|---|---|---|---|---|
| 71 | —CH₂—CH=CH₂ | H | 0 | — |
| 72 | —CH₂—C(CH₃)=CH₂ | H | 0 | — |
| 73 | —CH₂—CH=CH₂ | CHO | 0 | — |
| 74 | —CH₂—CH=CH₂ | CH₃ | 0 | — |

TABLE 2-continued (I-6)

[structure: pyrimidine-like ring with Z-N, CH₂S(O)ⱼ-X, NO₂, CH₂-N, S, N, Cl substituents]

| Compound No. | X | Z | j | Physical properties |
|---|---|---|---|---|
| 75 | —CH₂—Si(CH₃)(CH₃)—C₆H₅ | H | 0 | — |
| 76 | —CH₂C₆H₅ | H | 0 | — |
| 77 | —CH₂CH₂SCH₃ | H | 0 | — |

The compounds of the present invention show excellent activities as active ingredients for insecticides, miticides, nematicides and soil pesticides. For instance, they are effective against plant parasitic mites such as two-spotted spider mite (*Tetranychus urticae*), carmine spider mite (*Tetranychus cinnabarinus*) or citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus qrandis*), gypsy moth (*Lymantria dispar*), cucurbit leaf beetle (*Aulacophora femoralis*), aphids, planthoppers, leafhoppers, scales, bugs, whiteflies, thrips, grasshoppers, anthomyiid flies, scarabs, black cutworm (*Agrotis ipsilon*), cutworm (*Agrotis seqetum*) or ants; hygienic insect pests such as tropical rat mite (*Ornithonyssus bacoti*), cockroaches, housefly (*Musca domestica*) or house mosquito (*Culex pipiens pallens*); stored grain insect pests such as angoumois grain moth (*Sitotroga cerealella*), azuki bean weevil (*Callosobruchus chinensis*), confused flour beetle (*Tribolium confusum*) or mealworms; household goods insect pests such as casemaking clothes moth (*Tinea pellionella*), black carpet beetle (*Anthrenus scrophularidae*) or subterranean termites; and other parasites on domestic animals such as fleas, lice or flies. Further, they are also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus liqnicolus*). Furthermore, they are effective also against the soil pests. The soil pests in the present invention are gastropods such as slugs or snails, or isopods such as pillbugs or sowbugs. Still further, they are effective also against mites having the resistance to dicofol and organophosphorus insecticides and against insect pests such as aphids, leafhoppers and housefly having the resistance to organophosphorus, carbamate and/or synthetic pyrethroide insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

When used as active ingredients for insecticides, miticides, nematicides or soil pesticides, the compounds of the present invention may be formulated together with agricultural adjuvants into various forms such as dusts, granules, wettable powders, emulsifiable concentrates, soluble concentrates, water soluble powders, aerosols or pastes, just like conventional agricultural chemicals. When such formulations are to be actually used, they may be used as they are or after being diluted with suitable diluents such as water to a predetermined concentration.

Such formulations are usually composed of 0.1–90 parts by weight of active ingredient and 10–99.9 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay or alumina. As the liquid carriers, there may be mentioned water; alcohols such as isopropyl alcohol or ethylene glycol; ketones such as cyclohexanone or methyl ethyl ketone; ethers such as dioxane or tetrahydrofuran; aliphatic hydrocarbons such as kerosine gas oil or the like; aromatic hydrocarbons such as xylene, trimethylbenzene, tetramethylbenzene, methylnaphthalene or solvent naphtha; halogenated hydrocarbons such as chlorobenzene; acid amides such as dimethylacetamide; esters such as glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, 2,2-dichlorovinyl dimethyl phosphate, ethyl 3-methyl-4-(methylthio)phenyl isopropylphosphoramidate, O,O-dimethyl O-4-nitro-m-tolyl phosphorothioate, O-ethyl O-(4-nitrophenyl) phenylphosphonothioate, O,O-diethyl O-2-isopropyl-6-methylpyrimidin-4-yl phosphorothioate, O,O-dimethyl O-(3,5,6-trichloro-2-pyridyl) phosphorothioate, O,S-dimethyl acetylphosphoramidothioate, O-(2,4-dichlorophenyl) O-ethyl S-propyl phosphorodithioate or (RS)-S-sec-butyl O-ethyl 2-oxo-1,3-thiazolydin-3-yl phosphonothioate; carbamate compounds such as 1-naphthyl methylcarbamate, 2-isopropoxyphenyl methylcarbamate, 2-methyl-2-(methylthio)propionaldehyde O-methylcarbamoyloxime, 2,3-dihydro-2,2-dimethylbenzofuran- 7-yl methylcarbamate, dimethyl N,N'-[thiobis{(methylimino)carbonyloxy}] bisethanimidothioate, S-methyl N-(methylcarbamoyloxy) thioacetoimidate, N,N-dimethyl-2-methylcarbamoyloxyimino-2-(methylthio)acetamide, 2-(ethylthiomethyl)phenyl methylcarbamate, 2-dimethylamino-5,6-dimethylpyrimidin-4-yl dimethylcarbamate or 2-sec-butylphenyl methylcarbamate; nereistoxin derivatives such as S,S'-2-dimethyl aminotrimethylene bis(thiocarbamate) or N,N-dimethyl-1,2,3-trithian-5-yl amine; organic chlorine compounds such as 2,2,2-trichloro-1,1-bis(4-chlorophenyl)ethanol or 4-chlorophenyl-2,4,5-trichlorophenyl sulfone; organic metal compounds such as bis[tris(2-methyl-2-phenylpropyl)tin]oxide; pyrethroide compounds such as (RS)-α-cyano-3-phenoxybenzyl (RS)-2-(4-chlorophenyl)-3-methylbutyrate, 3-phenoxybenzyl (1RS)-cis,trans-3-(2,2-dichlorovinyl)-2,2-dimethylcyclopropanecarboxylate, (RS)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (1RS)-cis,trans-3-(2-chloro-3,3,3-trifluoropropenyl)-2,2-dimethylcyclopropanecarboxylate 4-methyl-2,3,5,6-tetrafluorobenzyl-3-(2-chloro-3,3,3-trifluoro-1-propenyl)-2,2-dimethylcyclopropane carboxylate or 2-(4-ethoxyphenyl)-2-methylpropyl 3-phenoxybenzyl ether; benzoyl urea compounds such as 1-(4-chlorophenyl)-3-(2,6-difluorobenzoyl)urea, 1-[3,5-dichloro-4-(3-chloro-5-trifluoromethyl-2-pyridyloxy)phenyl]-3-(2,6-difluorobenzoyl)urea or 1-(3,5-dichloro-2,4-difluorophenyl)-3-(2,6-difluorobenzoyl)urea; juvenile hormone-like compounds such as isopropyl(2E,4E)-11-methoxy-3,7,11-trimethyl-2,4-dodecadienoate; pyridazinone compounds such as 2-tert-butyl-5-(4-tertbutylbenzylthio)-4-chloro-3(2H)-pyridazinone; pyrazole compounds such as tert-butyl 4-[{1,3-dimethyl-5-phenoxypyrazol-4-yl}methylene aminooxymethyl benzoate; dinitro compounds; organic sulfur compounds; urea compounds; triazine compounds; hydrazine compounds; and other compounds such as 2-tert-butylimino-3-isopropyl-5-phenyl-3,4,5,6-tetrahydro-2H-1,3,5-thiadiazin-4-one, trans (4-chlorophenyl)-N-cyclohexyl-4-methyl-2-oxothiazolizinon-3-carboxamide, N-methylbis(2,4-xylyliminomethyl)amine, N'-(4-chloro-o-tolyl)-N,N-dimethylformamidine or (4-ethoxyphenyl)-[3-(4-fluoro-3-phenoxyphenyl)propyl](dimethyl)silane. Further, microbial insecticides such as *Bacillus thuriqiensis* agent or nuclear polyhedrosis virus; antibiotics such as avermectin or milbemycin; or the like may also be used in combination with the compounds of the present invention.

As the fungicides, there may be mentioned organophosphorus compounds such as S-benzyl O,O-diisopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloroisophthalonitrile; dithiocarbamate compounds such as polymeric manganese ethylenebis(dithiocarbamate), polymeric zinc ethylenebis(dithiocarbamate), manganese ethylenebis(dithiocarbamate) complex with zinc salt, dizinc bis(-dimethyldithiocarbamate)ethylenebis(dithiocarbamate) or polymeric zinc propylenebis(dithiocarbamate); N-halogenothioalkyl compounds such as 3a,4,7,7a-tetrahydro-N-(trichloromethylsulfenyl)phthalimide, 3a,4,7,7a-tetrahydro-N-(1,1,2,2-tetrachloroethylsulfenyl)phthalimide or N-(trichloromethylsulfenyl)phthalimide; dicarboxy imide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione or N-(3,5-dichlorophenyl)-1,2-dimethylcyclopropane-1,2-dicarboximide; benzimidazole compounds such as methyl 1-(butylcarbamoyl)-benzimidazol-2-yl-carbamate or dimethyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl)butan-2-ol, 1-[N-(4-chloro-2-trifluoromethylphenyl)-2-propoxyacetoimidoyl]imidazole, 1-[2-(2,4-dichlorophenyl)-4-ethyl-1, 3-dioxolan-2-ylmethyl] -1H-1,2,4-triazole, 1-[2-(2,4-dichlorophenyl)-4-propyl-1,3-dioxolan-2-ylmethyl]-1H-1,2,4-triazole or 1-[2-(2,4-dichlorophenyl)pentyl]-1H-1,2,4-triazole; carbinol compounds such as 2,4'-dichloro-α-(pyrimidin-5-yl)benzhydryl alcohol or (±)-2,4'-difluoro-α-(1H-1,2,4-triazol-1-ylmethyl)benzhydryl alcohol; benzanilide compounds such as 3'-isopropoxy-o-toluanilide or α,α,α-trifluoro-3'-isopropoxy-o-toluanilide; phenylamide compounds such as methyl N-(2-methoxyacetyl)-N-(2,6-xylyl)-DL-alaninate; pyridinamine compounds such as 3-chloro-N-(3-chloro-2,6-dinitro-4-α,α,α-trifluorotolyl)-5-trifluoromethyl-2-pyridinamine; piperazine compounds; morpholine compounds; anthraquinone compounds; quinoxaline compounds; crotonic acid compounds; sulfenic acid compounds; urea compounds and other compounds such as diisopropyl 1,3-dithiolan-2-ylidenemalonate, 5-methyl-1,2,4-triazolo[3,4-b]benzothiazole, 1,2,5,6-tetrahydropyrrolo[3,2,1-ij]quinolin-4-one, 6-(3,5-dichloro-4-methylphenyl)-3(2H)-pyridazinone, 3-allyloxy-1,2-benzisothiazole-1,1-dioxide or 1-(4-chlorobenzyl)-1-cyclopentyl 3-phenylurea. Further, antibiotic substances such as validamycin A may also be used in combination with the compounds of the present invention.

The insecticides, miticides, nematicides and soil pesticides of the present invention are applied in an active ingredient concentration of from 0.1 to 20,000 ppm, preferably from 1 to 2,000 ppm. The active ingredient concentration may optionally be changed depending upon the formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 10 to 1,000 g, per hectare. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

-continued

| | |
|---|---|
| (d) Xylene | 50 parts by weight |

The above components are uniformly mixed and dissolved to obtain an emulsifiable concentrate.

FORMULATION EXAMPLE 4

| | |
|---|---|
| (a) Kaoline | 68 parts by weight |
| (b) Sodium lignin sulfonate | 2 parts by weight |
| (c) Polyoxyethylenealkylaryl sulfate | 5 parts by weight |
| (d) Fine silica powder | 25 parts by weight |

A mixture of the above components was mixed with Compound No. 3 in a weight ratio of 4:1 to obtain a wettable powder.

FORMULATION EXAMPLE 5

| | |
|---|---|
| (a) Compound No. 8 | 50 parts by weight |
| (b) Oxylated polyalkylphenyl phosphate-triethanolamine | 2 parts by weight |
| (c) Silicone | 0.2 part by weight |
| (d) Water | 47.8 parts by weight |

The above components were uniformly mixed and pulverized to obtain a base liquid, and

| | |
|---|---|
| (e) Sodium polycarboxylate | 5 parts by weight |
| (f) Anhydrous sodium sulfate | 42.8 parts by weight | were added, and the mixture was uniformly mixed and dried to obtain a dry flowable.

FORMULATION EXAMPLE 6

| | |
|---|---|
| (a) Compound No. 21 | 5 parts by weight |
| (b) Polyoxyethyleneoctylphenyl ether | 1 part by weight |
| (c) Phosphoric acid ester of polyoxyethylene | 0.5 part by weight |
| (d) Granular calcium carbonate | 93.5 parts by weight |

The above components (a) to (c) were uniformly mixed and kneaded together with a small amount of acetone, and then the mixture was sprayed onto the component (d) to remove acetone, thus obtaining granules.

FORMULATION EXAMPLE 7

| | |
|---|---|
| (a) Component No. 25 | 2.5 parts by weight |
| (b) N-methyl-2-pyrrolidone | 2.5 parts by weight |
| (c) Soybean oil | 95.0 parts by weight |

The above components are uniformly mixed and dissolved to obtain an ultra low-volume formulation.

FORMULATION EXAMPLE 8

| | |
|---|---|
| (a) Compound No. 37 | 5 parts by weight |
| (b) N,N'-dimethylacetamide | 15 parts by weight |
| (c) Polyoxyethylenealkyl aryl ether | 10 parts by weight |
| (d) Xylene | 70 parts by weight |

The above components are uniformly mixed to obtain an emulsifiable concentrate.

FORMULATION EXAMPLE 9

| | |
|---|---|
| (a) Component No. 3 | 20 parts by weight |
| (b) Sodium laurylsulfate | 3 parts by weight |
| (c) Water-soluble starch | 77 parts by weight |

The above components were uniformly mixed to obtain a water soluble powder.

We claim:

1. An imidazolidine derivative having the formula (I) or its salt:

$$\begin{array}{c} Z \\ | \\ N \\ \diagup \quad \diagdown \\ \quad \quad \quad \diagup C-CH_2S(O)_j-X \\ \diagdown \quad \diagup \\ N \quad NO_2 \\ | \\ CH_2-Y \end{array} \quad (I)$$

wherein X is $C_2$-$C_6$ alkenyl group or $C_2$-$C_6$ alkynyl group in which the alkenyl or alkynyl group may be substituted with a halogen atom or $$\begin{array}{c} Z \\ | \\ N \\ \diagup \quad \diagdown \\ \quad \quad \quad \diagup C-CH_2S(O)_j- \\ \diagdown \quad \diagup \\ N \quad NO_2 \\ | \\ CH_2-Y \end{array}$$

group, or $$a-(\overset{R^1}{\underset{R^2}{C}})_k-(\overset{R^3}{\underset{R^4}{C}})_l-(\overset{O}{\overset{\|}{C}})_m-(W)_n-R^5 \quad \text{group}$$

in which each or $R^1$, $R^2$, $R^3$ and $R^3$ is independently a hydrogen atom or $C_1$-$C_6$ alkyl group; $R^5$ is $C_1$-$C_6$ alkyl group which may be substituted with a halogen atom; $C_3$-$C_6$ cyclo alkyl group which may be substituted with a halogen atom, $C_1$-$C_6$ alkyl group or halo $C_1$-$C_6$ alkyl group; a phenyl group which may be substituted with a substituent selected from the group consisting of a halogen atom, $C_1$-$C_6$ alkyl group, $C_2$-$C_6$ alkenyl group, $C_2$-$C_6$ alkynyl group, $C_1$-$C_6$ alkoxy group, $C_1$-$C_6$ alkoxycarbonyl group in which the alyl, alkenyl, alkynyl, alkoxy or alkoxycarbonyl group may be substituted with a halogen atom, phenoxy group, phenyl group and pyridyloxy group in which the phenoxy, phenyl or pyridyloxy group may be substituted with a halogen atom, $C_1$-$C_6$ alkyl group or halo $C_1$-$C_6$ alkyl group; W is an oxygen atom or a sulfur atom; and each of k, l, m and n is independently an integer of 0 or 1, provided that (a) case where all of k, l and m are 0 at the same time and (b) case where m and n are 0 at the same time and $R^5$ is $C_1$-$C_6$ alkyl group which may be substituted with a halogen atom, are excluded, or $$a-\overset{R^6}{\underset{R^7}{C}}-\overset{R^8}{\underset{R^9}{Si}}-R^{10}$$

group in which each of $R^6$ and $R^7$ is independently a hydrogen atom or $C_1$-$C_6$ alkyl group; each of $R^8$ and $R^9$ is independently $C_1$-$C_6$ alkyl group; $R^{10}$ is a $C_1$-$C_6$ alkyl group which may be substituted with a halogen atom or a phenyl group; a phenyl group, a naphthyl group or a pyridyl group in which the phenyl, naphthyl or pyridyl group may be substituted with the same substituents as mentioned in the phenyl group as $R^5$, $C_2$-$C_6$ alkenyl group or $C_2$-$C_6$ alkynyl group in which the alkenyl or alkynyl group may be substituted with a halogen atom; Y is a 6-chloro-3-pyridyl group Z is a hydrogen atom, $C_1$-$C_6$ alkyl group or $C_1$-$C_6$ acyl group; and j is 0.

2. The imidazolidine derivative or its salt according to claim 1, wherein Y is a 6-chloro-3-pyridyl group.

3. The imidazolidine derivative or its salt according to claim 1, wherein j is 0.

4. The imidazolidine derivative or its salt according to claim 1, wherein Y is a 6-chloro-3-pyridyl group, and j is 0.

5. The imidazolidine derivative or its salt according to claim 1, wherein X is an allyl group; Y is a 6-chloro-3-pyridyl group; Z is a hydrogen atom; and j is 0.

6. The imidazolidine derivative or its salt according to claim 1, wherein X is a 2-methyl-2-propenyl group; Y is a 6-chloro-3-pyridyl group; Z is a hydrogen atom; and j is 0.

7. The imidazolidine derivative or its salt according to claim 1, wherein X is a dimethylphenylsilylmethyl group; Y is a 6-chloro-3-pyridyl group; Z is a hydrogen atom; and j is 0.

8. The imidazolidine derivative or its salt according to claim 1, selected from the group consisting of 1-(6-chloro-3-pyridylmethyl)-2-(1-nitro-2-benzylthioethylidene)imidazolidine, 1-(6-chloro-3-pyridylmethyl)-2-(1-nitro-2-allylthioethylidene)imidazolidine, 1-(6-chloro-3-pyridylmethyl)-2-(1-nitro-2-ethylthioethylidene)imidazolidine, 1-(6-chloro-3-pyridylmethyl)-2-[1-nitro-2-(2-methyl-2-propenyl)thioethylidene]imidazolidine, 1-(6-chloro-3-pyridylmethyl)-2-[1-nitro-2-(2-propynyl)thioethylidene]imidazolidine, 1-(6-chloro-3-pyridylmethyl)-2-(1-nitro-2-dimethyl(phenylsilylmethylthioethylidene)imidazolidine and 1-(6-chloro-3-pyridylmethyl)-2-[1-nitro-2-(2-butynyl)thioethylidene]imidazolidine.

9. A pesticidal composition comprising a pesticidally effective amount of an imidazolidine derivative or its salt and an agriculturally acceptable adjuvant, the imidazolidine derivative having the formula (I) as defined in claim 1.

* * * * *

UNITED STATES PATENT AND TRADEMARK OFFICE
CERTIFICATE OF CORRECTION

PATENT NO. : 5,256,674
DATED : October 26, 1993
INVENTOR(S) : Haga et al

It is certified that error appears in the above-indentified patent and that said Letters Patent is hereby corrected as shown below:

Columns 23 and 24 should be inserted in the soft copy as per attached sheet.

Signed and Sealed this

Twenty-eighth Day of June, 1994

Attest:

BRUCE LEHMAN

*Attesting Officer*          *Commissioner of Patents and Trademarks*

TEST EXAMPLE 1

Insecticidal test against small brown rice planthopper
(*Laodelphax striatellus*)

A rice seedling was dipped in a dispersion containing each active ingredient in a concentration of 800 ppm for 10 seconds, then dried in air and put into a test tube with the root portion enclosed by absorbent cotton. Then, 10 larvae of small brown rice planthopper (*Laodelphax striatellus*) were released in the test tube, and the mouth of the test tube was covered with a piece of gauze. Then, the test tube was kept in a constant temperature chamber with lightening at 26° C. At 5 days after the release, dead insects were counted, and the mortality was calculated in accordance with the following equation.

$$\text{Mortality (\%)} = \frac{\text{Number of dead insects}}{\text{Number of insects released}} \times 100$$

As this result, the mortality was 100% with each of Compounds Nos. 1–10, 17, 20–40, 53, 55–57 and 59–65.

TEST EXAMPLE 2

Insecticidal test against green rice leafhopper
(*Nephotettix cincticeps*)

The same test as in Test Example 1 was carried out, except that the larvae of small brown rice planthopper were replaced by those of green rice leafhopper (*Nephotettix cincticeps*).

As this result, the mortality was 100% with each of Compounds Nos. 1–5, 8, 9, 20–26, 30, 54–56, 61 and 63.

TEST EXAMPLE 3

Insecticidal test against green peach aphid (*Myzus persicae*)

Each formulation containing an active ingredient was dispersed in water to obtain a dispersion of each active ingredient having a concentration of 800 ppm. The petiole of each of eggplants with only one foliage leaf left (planted in a pot having a diameter of 8 cm and a height of 7 cm) was coated with a sticker, and about 2–3 apterous viviparous female of green peach aphid (*Myzus persicae*) were infested and incubated on the foliage leaf of the eggplant. After two days from the infestation, the adult insects were removed and the number of larvae was counted. Then, the foliage leaf of the eggplant infested with the larvae was dipped in the above prepared dispersion having the predetermined concentration for about 10 seconds, then dried in air and kept in a constant temperature chamber with lightening at 26° C. On the 5th day after the treatment, dead insects were counted, and the mortality was calculated by the following equation.

$$\text{Mortality (\%)} = \frac{\text{Number of dead insects}}{\text{Number of treated insects}} \times 100$$

The insects released from the leaf were counted as dead insects.

As this result, the mortality was 100% with each of Compounds Nos. 1–10, 17, 20–26, 29–40, 53–62, 64 and 65.

TEST EXAMPLE 4

Penetration and translocation test against green peach aphid (*Myzus persicae*)

Each formulation containing an active ingredient was dispersed in water to obtain a dispersion of each active ingredient having a concentration of 800 ppm. The petiole of each of eggplants with only one foliage leaf left (planted in a pot having a diameter of 8 cm and a height of 7 cm) was coated with a sticker, and about 2–3 apterous viviparous female of green peach aphid (*Myzus persicae*) were infested and incubated to the foliage leaf of the eggplant. After two days from the infestation, the adult insects were removed and the number of larvae was counted. Then, the eggplant infested with the larvae was treated by drenching 10 ml of the above prepared dispersion having the predetermined concentration into the soil in the pot, and was kept in a constant temperature chamber with lightening at 26° C. On the 5th day after the treatment, dead insects were counted, and the mortality was calculated in the same manner as in Test Example 3.

The insects released from the leaf were counted as dead insects.

As this result, the mortality was 100% with each of Compounds Nos. 1–10, 17, 20–26, 29–37, 53–60 and 62–65.

TEST EXAMPLE 5

Insecticidal test against common cutworm (*Spodoptera litura*)

Each formulation containing an active ingredient was dispersed in water to obtain a dispersion of each active ingredient having a concentration of 800 ppm. Leaves of cabbage were dipped in the respective dispersion for about 10 seconds, and then dried in air. A sheet of moistened filter paper was placed in a Petri dish having a diameter of 9 cm, and the dried leaves of cabbage were put on the filter paper. 10 Larvae of common cutworm (*Spodoptera litura*) in second or third instar were released on the leaves, and the Petri dishes were covered and kept in a constant temperature chamber with lightening at a temperature of 26° C. On the 5th day after release, dead insects were counted, and the mortality was calculated in the same manner as in Test Example 1.

As this result, the mortality was 100% with each of Compounds Nos. 1–10, 17, 20–40, 53–58, 60–62, 64 and 65.

Now, the Formulation Examples of the present invention will be described. However, the compounds of the present invention, the amount of the active ingredients of the types of the formulations are not restricted to these specific Examples.

FORMULATION EXAMPLE 1

| | |
|---|---|
| (a) Compound No. 1 | 20 parts by weight |
| (b) Kaolin | 72 parts by weight |
| (c) Sodium lignin sulfonate | 8 parts by weight |

The above components are uniformly mixed to obtain a wettable powder.

FORMULATION EXAMPLE 2

| | |
|---|---|
| (a) Compound No. 2 | 5 parts by weight |
| (b) Talc | 95 parts by weight |

The above components are uniformly mixed to obtain a dust.

FORMULATION EXAMPLE 3

| | |
|---|---|
| (a) Compound No. 4 | 20 parts by weight |
| (b) N,N-dimethylacetamide | 20 parts by weight |
| (c) Polyoxyethylenealkylphenyl ether | 10 parts by weight |